United States Patent
Bae et al.

(10) Patent No.: US 6,887,484 B2
(45) Date of Patent: May 3, 2005

(54) VACCINE COMPOSITION CONTAINING A PROMOTER PEPTIDE

(75) Inventors: Yoe-Sik Bae, Koryung-gun (KR);
Youn-Dong Kim, Pohang-si (KR);
You-Suk Seo, Pohang-si (KR);
Young-Chul Sung, Pohang-si (KR);
Pann-Ghill Suh, Pohang-si (KR);
Sung-Ho Ryu, Pohang-si (KR);
Taehoon Lee, Pohang-si (KR)

(73) Assignees: Posco (KR); Pohang University of Science & Technology (KR)

( * ) Notice: Subject to any disclaimer, the term of this patent is extended or adjusted under 35 U.S.C. 154(b) by 86 days.

(21) Appl. No.: 10/209,802

(22) Filed: Jul. 31, 2002

(65) Prior Publication Data
US 2003/0091585 A1 May 15, 2003

Related U.S. Application Data
(60) Provisional application No. 60/309,068, filed on Jul. 31, 2001.

(51) Int. Cl.⁷ .................. A61K 45/00; A61K 33/00; A61K 39/29; A61K 39/12; A61K 39/02
(52) U.S. Cl. ............... 424/278.1; 424/184.1; 424/185.1; 424/228.1; 424/225.1; 424/209.1; 424/247.1; 424/245.1; 424/254.1; 424/212.1; 424/219.1; 424/217.1; 424/244.1; 424/229.1; 424/256.1; 424/224.1; 424/211.1

(58) Field of Search ............... 424/278.1, 184.1, 424/185.1, 222.1, 225.1, 209.1, 247.1, 245.1, 254.1, 212.1, 219.1, 217.1, 244.1, 229.1, 256.1, 224.1, 211.1, 228.1, 226.1, 227.1, 231.1, 232.1, 240.1, 239.1, 238.1; 514/17

(56) References Cited
U.S. PATENT DOCUMENTS
2003/0055001 A1 * 3/2003 Bae et al. ................ 514/17

FOREIGN PATENT DOCUMENTS
WO       01/57074    *  8/2001    ........... C07K/14/16

OTHER PUBLICATIONS
Forns et al (Journal of Hepatology 37:684–695, 2002).*
Bae et al (Journal of Leukocyte Biology 66:915–922, 1999).*
Yang et al (Journal of Leukocyte Biology 69:691–697, 2001).*
Gao et al (Journal of Experimental Medicine 189:657–662, 1999).*

* cited by examiner

Primary Examiner—Mary E. Mosher
(74) Attorney, Agent, or Firm—Anderson Kill & Olick, PC

(57) ABSTRACT

A vaccine having a good vaccination effect, which comprises an antigen; a peptide selected from the group consisting of a peptide having the amino acid sequence of SEQ ID NO: 1, a peptide having the amino acid sequence of SEQ ID NO: 2, and a peptide derived from a peptide having the amino acid sequence of SEQ ID NO: 1 or SEQ ID NO: 2; and an immune activator.

11 Claims, 1 Drawing Sheet

VACCINE COMPOSITION CONTAINING A PROMOTER PEPTIDE

CROSS REFERENCE TO RELATED APPLICATIONS

This application claims the benefit under 35 U.S.C. §119(e) of the U.S. Provisional Application Ser. No. 60/309,068, entitled "VACCINE CONTAINING A PROMOTER PEPTIDE", filed Jul. 31, 2001.

BACKGROUND OF THE INVENTION (a) Field of the Invention

The present invention relates to a vaccine composition containing a promoter peptide, and more specifically to a vaccine containing a specific peptide that promotes the vaccination effect.

(b) Description of the Related Art

The essence of the immune system is its capacity to recognize foreign substances, or antigens. Various antigen-specific B-lymphocytes are on the alert, and when a foreign antibody invades the body, certain B-lymphocytes are activated upon recognizing the antigen to trigger the so-called primary immune response, which involves the transfer of intracellular signals and secretion of a specific antibody against the antigen. Some of the activated B-lymphocytes persist as memory cells which retain the capacity to produce the antibody upon stimulation by the same antigen. Thus when the antigen is encountered a second time, a secondary immune response takes place, and memory cells quickly produce a large amount of the antibody.

Injection of a vaccine containing an antigen artificially induces the immune response by stimulating the immune system with the injected antigen. In this case, an immune activator such as alum (aluminum hydroxide) or Freund's adjuvant is added to nonspecifically enhance the immune response to the vaccine.

The present inventors have previously reported that the peptide of SEQ ID NO: 1 activates monocytes, B-lymphocytes, and neutrophils (Beak, S. H. et al., *J. Biol. Chem.*, 271, 8170 (1996)). This peptide enhances the activity of phospholipase C (PLC), an intracellular signal transduction protein in B-lymphocytes, and the activated PLC catalyzes the hydrolysis of phosphatidylinositol 4,5-bisphosphate ($PIP_2$) into two intracellular second signal messengers, inocytol 1,4,5-trisphosphate ($IP_3$) and diacylglycerol (DAG). The $IP_3$ induces an increase in intracellular free calcium concentration ($[Ca^{2+}]_i$), while DAG directly activates protein kinase C (Nixhizuka Y., et al., *Science*, 233, 305 (1986)). It has been reported that the peptide induces the intracellular calcium $[Ca^{2+}]_i$ release in a human B-lymphocyte cell line U266 (Baek, S. H., et al., J. Biol. Chem., 271, 8170 (1990)) and activates the cellular signal pathway by binding with a specific receptor protein in the cell membrane of the U266 cell line (Seo, J. K., et al., *J. Immunol.*, 158, 1895(1997)). Further, the peptide is capable of stimulating neutrophils to increase the production of active oxygen species, which enhances the sterilization effect (Bae, Y. S., et al., *J. Leukoc. Biol.*, 65, 241 (1999)), and induces chemotaxis of human neutrophils.

The Hepatitis C virus (HCV), discovered in 1989, is an RNA virus, and chronic infection by the virus can lead to hepatomas. However, at present, there is no effective cure for individuals infected with HCV, and even the identity and specificity of HCV have not been completely understood. Therefore, a need to develop an improved vaccine which can prevent various diseases such as HCV infection has continued to exist.

SUMMARY OF THE INVENTION

It is an object of the present invention to provide a vaccine composition having an improved vaccination effect.

It is another object to provide a method for enhancing an antigen-specific cell-mediated immune response which comprises administering an amount of an immunomodulator as a vaccine adjuvant to an individual, wherein said amount of immunomodulator causes an enhanced antigen-specific cell-mediated immune response as compared to an antigen-specific cell-mediated immune response seen in the absence of said immunomodulator.

It is still another object to provide a method for enhancing an antigen-specific CD4 T-cell function response which comprises administering an amount of an immunomodulator as a vaccine adjuvant to an individual, wherein said amount of immunomodulator causes an enhanced antigen-specific CD4 T-cell function response as compared to an antigen-specific CD4 T-cell function response seen in the absence of said immunomodulator.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawing, which is incorporated in and constitutes a part of the specification, illustrates an embodiment of the invention, and together with the description, serves to explain the principles of the invention.

DETAILED DESCRIPTION OF THE PREFERRED EMBODIMENTS

Figure 1:
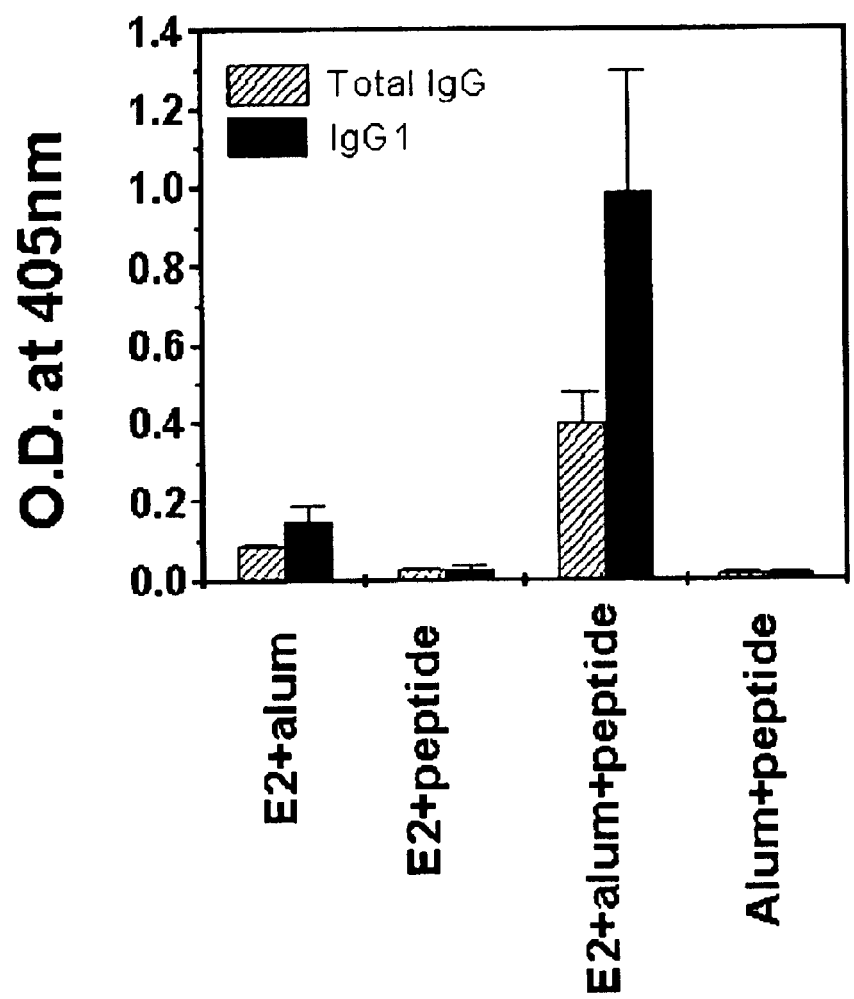
FIG. 1 shows the amounts of antibodies generated in the blood of test animals in response to the administration of the inventive and comparative vaccine compositions.

In accordance with one aspect of the present invention, there is provided a vaccine composition comprising: a specific antigen, wherein an amount of said specific antigen causes an immune response; a peptide selected from the group consisting of a peptide having the amino acid sequence of SEQ ID NO: 1, a peptide having the amino acid sequence of SEQ ID NO: 2, and a peptide derived from a peptide having the amino acid sequence of SEQ ID NO: 1 or SEQ ID NO: 2; and an immune activator, in a physiologically acceptable carrier.

The antigen that may be advantageously used in the composition of the present invention is one of specific antigens that cause an immune response. The antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus, or rabies.

The antigen can preferably be a viral protein or a recombinant protein. Exemplary viral proteins include hepatitis C virus (HCV) proteins such as HCV E2 protein, E1 protein, and a mixture thereof, but these do not limit the scope of the invention. The total amount of the antigen used in the inventive composition may range from 0.001 to 1 wt %, preferably from 0.002 to 0.007 wt %, and most preferably from 0.003 to 0.005 wt % based on the total weight of the composition.

The peptide that may be advantageously used in the composition of the present invention consists of 6 amino acids, and it has the amino acid sequence of SEQ ID NO: 1 (Trp Lys Tyr Met Val Met) or SEQ ID NO: 2 (Thr Lys Tyr Met Val Met). The peptide Met at the C-terminal is preferably a D-methionine residue. The peptide is also a peptide derivatives of the peptide of SEQ ID NO: 1 or SEQ ID NO: 2 having an amino acid substituent. For example, the methionine residue of SEQ ID NO: 1 or SEQ ID NO: 2 preferably has $CONH_2$ substituted for the carboxyl group.

The peptide of the present invention can be synthesized using a conventional peptide synthesis method (Houghten, R. A. et al., *Nature*, 354, 84(1991)). The total amount of the peptide used in the inventive composition may range from 0.001 to 1 wt %, preferably from 0.002 to 0.007 wt %, and most preferably from 0.003 to 0.005 wt % based on the total weight of the composition.

Exemplary immune activators that may be used in the composition of the present invention include aluminum hydroxide (alum), Freund's adjuvant, and a mixture thereof, but these do not limit the scope of the invention. The total amount of the immune activator used in the inventive composition may range from 0.001 to 0.01 wt %, and preferably from 0.006 to 0.008 wt % based on the total weight of the composition.

In accordance with another aspect of the present invention, a vaccine composition is provided that comprises an HCV E2 protein; a peptide selected from the group consisting of a peptide having the amino acid sequence of SEQ ID NO: 1, a peptide having the amino acid sequence of SEQ ID NO: 2, and a peptide derived from a peptide having the amino acid sequence of SEQ ID NO: 1 or SEQ ID NO: 2; and an immune activator, in a physiologically acceptable carrier.

The vaccine of the present invention may further comprise a soluble excipient which is selected from those known in the art, e.g., a carbohydrate, a protein, an amino acid, a fatty acid, a mineral salt, a surfactant, polyethylene glycol, or a mixture thereof, to increase the stability of the antigen. The carbohydrate which may be suitably used in the present invention includes a soluble saccharide such as hydropropyl cellulose, carboxymethyl cellulose, sodium carboxymethyl cellulose, hyaluronic acid, chitosan, alginate, glucose, xylose, galactose, fructose, maltose, saccharose, dextran, and chondroitin sulfate. The protein which may be suitably used in the present invention includes albumin and gelatin, and exemplary amino acids for use in the present invention include glycine, alanine, glutamic acid, arginine, lysine, and a salt thereof.

The vaccine composition of the present invention can be administered via various routes including oral, subcutaneous, intravenous, and intramuscular introduction. However, it should be understood that the amount of the active ingredient actually administered ought to be determined in light of various relevant factors including the condition to be treated, the chosen route of administration, the age, sex, and body weight of the individual patient, and the severity of the patient's symptom. Therefore, the above does not limit the scope of the invention in any way.

In the present invention, the peptide and the immune activator work together to generate a remarkable synergistic effect of enhancing the vaccination effect, and the inventive composition induces the antibody formation to a level which is much higher than that achievable with any of the conventional compositions.

In accordance with still another aspect of the present invention, a method for enhancing an antigen-specific cell-mediated immune response is provided which comprises administering an amount of an immunomodulator as a vaccine adjuvant to an individual, wherein said amount of immunomodulator causes an enhanced antigen-specific cell-mediated immune response as compared to an antigen-specific cell-mediated immune response seen in the absence of said immunomodulator, said immunomodulator being a peptide selected from the group consisting of a peptide having the amino acid sequence of SEQ ID NO: 1, a peptide having the amino acid sequence of SEQ ID NO: 2, and a peptide derived from a peptide having the amino acid sequence of SEQ ID NO: 1 or SEQ ID NO: 2. The immunomodulator may be a compound derived from the peptide having the amino acid sequence of SEQ ID NO: 1 or SEQ ID NO: 2.

The immunomodulator is administered in a vaccine comprising an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus, or rabies.

The immunomodulator is administered up to three hours prior to or after vaccination, or contemporaneously with vaccination. The vaccine comprises an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus, or rabies. The immunomodulator is administered via an epicutaneous, intramuscular, intradermal, or subcutaneous route, but it is not limited thereto. The immunomodulator is preferably administered topically.

In accordance with yet another aspect of the present invention, a method for enhancing an antigen-specific CD4 T-cell function response is provided which comprises administering an amount of an immunomodulator as a vaccine adjuvant to an individual, wherein said amount of immunomodulator causes an enhanced antigen-specific CD4 T-cell function response as compared to an antigen-specific CD4 T-cell function response seen in the absence of said immunomodulator, said immunomodulator being a synthetic peptide selected from the group consisting of a peptide having the amino acid sequence of SEQ ID NO: 1, a peptide having the amino acid sequence of SEQ ID NO: 2, and a peptide derived from a synthetic peptide having the amino acid sequence of SEQ ID NO: 1 or SEQ ID NO: 2. The immunomodulator may be a compound derived from the peptide having the amino acid sequence of SEQ ID NO: 1 or SEQ ID NO: 2.

The immunomodulator is administered in a vaccine comprising an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus, or rabies.

The immunomodulator is administered up to three hours prior to or after vaccination, or contemporaneously with vaccination. The vaccination comprises administering an antigen which is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus, or rabies. The immunomodulator is administered via an epicutaneous, intramuscular, intradermal or subcutaneous route, but it is not limited thereto. The immunomodulator is preferably administered topically.

The following Reference Example and Examples are given for the purpose of illustration only, and are not intended to limit the scope of the invention.

REFERENCE EXAMPLE

Overexpression and Isolation of HCV E2 Proteins

To obtain HCV E2 protein, 10 mg of DNA of the pMT3-hGHE2 vector containing a fusion gene of HCV E2 and human growth hormone (hGH) (Lee, K. J., et al., *J. Biol. Chem.*, 272, 30040(1997)) was transformed into CHO (Chinese hamster ovary) cells which were incubated in an α-minimal essential medium (containing 10% fetal bovine serum, hyphoxantine, and thymidine), in accordance with the calcium phosphate precipitation method (Cho, Y. G. et al., *Mol. Cells*, 3, 195 (1993)).

The transformed CHO cells thus obtained were incubated in an α-minimal essential medium containing 5% dialyzed fetal bovine serum, and then the monolayer-cultured CHO cells were transferred to a free-serum medium and incubated for 72 hours to overexpress the fusion protein of HCV E2 and hGH.

The culture solution thus obtained was collected and subjected to hGH monoclonal antibody affinity column chromatography using a column (CNBr-activated Sepharose-4B, Pharmacia, Sweden) which was pre-equilibrated with a phosphate buffer solution (PBS) (pH 7.2). The column was washed with the same buffer containing 0.5N NaCl, then 10 mM of a sodium phosphate buffer containing 3M NaSCN was added to the column to elute E2 protein. The eluted E2 protein was dialyzed with PBS to obtain purified E2 protein.

EXAMPLE 1

Preparation and Injection of Vaccine

5 µg of E2 protein antigen obtained in Reference Example was dissolved in 150 µl of PBS (pH 7.2), and 7 µg of the peptide of sequence of SEQ ID NO: 1 synthesized using a conventional peptide synthesis method (Houghten, R. A. et al., *Nature*, 354, 84(1991)) was added thereto together with alum to obtain a vaccine.

The vaccine thus obtained was injected subcutaneously into test mice (6-8-week-old athymic nu/nu on a BALB/c background). After 5 weeks, a booster injection was carried out, and after another 2 weeks, blood samples were taken from the mice.

For comparison, three different vaccine compositions were also tested as above. These comparative controls were: a vaccine containing E2 protein and alum; a vaccine containing E2 protein and the peptide of sequence of SEQ ID NO: 1; and a vaccine containing alum and the peptide of sequence of SEQ ID NO: 1. The peptides used in this Example include the D-Met residue of SEQ ID NO: 1 having $CONH_2$ substituted for the carboxyl group.

EXAMPLE 2

Quantity of Antibody

The E2 protein antigen obtained in Reference Example was diluted to a concentration of 2 µg/ml and added to a 96-well plate (costar®) in an amount of 50 µl/well, and the plate was incubated at 4° C. overnight. Then, the 96-well plate was washed three times with PBS-Tween 20 (20 mM phosphate, 150 mM NaCl, 0.05% Tween 20, pH 7.2; PBS-T), and PBS-T containing 5% nonfat milk was added to the plate in an amount of 100 µl/well. The plate was kept at room temperature for 2 hours so as to prevent any non-specific reactions which might have occurred later. 50 µl each of the bloods samples (diluted 100-fold in volume) were added to each of the wells, and they were incubated at room temperature for 2 hours. After the reaction, the plate was washed three times with 200 µl/well of PBS-T, and a solution containing horseradish peroxidase (HRP)-conjugated goat anti-mouse antibody (total IgG or IgG type 1 (Ig G1), Kirkegaard & Perry Laboratories, U.S.A., diluted 5000-fold in volume using PBS-T containing 5% nonfat milk) was added to the wells in an amount of 50 µl/well. The resultant was incubated at room temperature for 2 hours and washed 5 times with 200 µl/well of PBS-T buffer.

Thereafter, 80 µl/well of color former (ABSI (Chemicon®)) were added to each of the 96-wells of the plate, and they were incubated at room temperature for 20 minutes. After the reaction, the O.D. of each well was determined at the wavelength of 405 nm with an ELISA reader.

The results shown in FIG. 1 reveal that the level of antibody formation achieved by injecting the inventive vaccine (E2 protein+peptide+alum) is much higher than those attained by using the comparative compositions. This suggests that the peptide of SEQ ID NO: 1 generates a remarkable synergistic effect of promoting the vaccination efficiency when it is used together with alum.

While the embodiments of the subject invention have been described and illustrated, it is obvious that various changes and modifications can be made therein without departing from the spirit of the present invention, which is be limited only by the scope of the appended claims.

What is claimed is:

1. A vaccine composition comprising: a specific antigen, wherein an amount of said specific antigen causes an immune response; a peptide selected from the group consisting of a peptide having the amino acid sequence of SEQ ID NO: 1, a peptide having the amino acid sequence of SEQ ID NO: 2, and a peptide derived from a peptide having the amino acid sequence of SEQ ID NO: 1 or SEQ ID NO: 2; and an immune activator, in a physiologically acceptable carrier.

2. The vaccine composition of claim 1, wherein the antigen is a viral protein.

3. The vaccine composition of claim 1, wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus, or rabies.

4. The vaccine composition of claim 1, wherein the antigen is a recombinant protein.

5. The vaccine composition of claim 1, wherein the antigen is a recombinant viral protein.

6. The vaccine composition of claim 1, wherein the antigen is an HCV protein.

7. The vaccine composition of claim 1, wherein the antigen is an HCV E2 protein.

8. The vaccine composition of claim 1, wherein the antigen is a recombinant HCV E2 protein.

9. A vaccine composition comprising: an HCV E2 protein; a peptide selected from the group consisting of a peptide having the amino acid sequence of SEQ ID NO: 1, peptide having the amino acid sequence of SEQ ID NO: 2, and a peptide derived from a peptide having the amino acid sequence of SEQ ID NO: 1 or SEQ ID NO: 2; and an immune activator, in a physiologically acceptable carrier.

10. The vaccine composition of claim 1, wherein the amount of the peptide ranges from 0.001 to 1 wt % based on the total weight of the vaccine.

11. The vaccine composition of claim 1, wherein the immune activator is aluminum hydroxide (alum), Freund's adjuvant, or a mixture thereof.

* * * * *

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: PEPTIDE PROMOTING VACCINATION EFFECT
<220> FEATURE:
<221> NAME/KEY: MOD_RES (modified residues)
<222> LOCATION: (6)
<223> OTHER INFORMATION: D-Met -continued

```
<220> FEATURE:
<221> NAME/KEY: SITE
<222> LOCATION: (6)
<223> OTHER INFORMATION: Methionine residue optionally substituted with
      -NH2 group on carboxyl group

<400> SEQUENCE: 1

Trp Lys Tyr Met Val Met
1               5

<210> SEQ ID NO 2
<211> LENGTH: 6
<212> TYPE: PRT
<213> ORGANISM: Artificial Sequence
<220> FEATURE:
<223> OTHER INFORMATION: PEPTIDE PROMOTING VACCINATION EFFECT
<220> FEATURE:
<221> NAME/KEY: MOD_RES (modified residues)
<222> LOCATION: (6)
<223> OTHER INFORMATION: D-Met
<220> FEATURE:
<221> NAME/KEY: SITE
<222> LOCATION: (6)
<223> OTHER INFORMATION: Methionine residue optionally substituted with
      -NH2 group on carboxyl group

<400> SEQUENCE: 2

Thr Lys Tyr Met Val Met
1               5
```